United States Patent
Jin et al.

(10) Patent No.: US 10,702,249 B2
(45) Date of Patent: Jul. 7, 2020

(54) WIRELESS PROBE AND METHOD FOR POWER CONTROLLING OF WIRELESS PROBE

(71) Applicants: SAMSUNG MEDISON CO., LTD., Gangwon-do (KR); SAMSUNG ELECTRONICS CO., LTD., Suwon-si, Gyeonggi-do (KR)

(72) Inventors: Gil-ju Jin, Hongcheon-gun (KR); Mi-jeoung Ahn, Hongcheon-gun (KR); Nam-woong Kim, Hongcheon-gun (KR); Seong-ho Chang, Hongcheon-gun (KR)

(73) Assignees: Samsung Medison Co., Ltd., Hongcheon-gun, Gangwon-do (KR); Samsung Electronics Co., Ltd., Suwon-si, Gyeonggi-do (KR)

( * ) Notice: Subject to any disclaimer, the term of this patent is extended or adjusted under 35 U.S.C. 154(b) by 617 days.

(21) Appl. No.: 14/634,448

(22) Filed: Feb. 27, 2015

(65) Prior Publication Data

US 2015/0245823 A1 Sep. 3, 2015

(30) Foreign Application Priority Data

Feb. 28, 2014 (KR) .................. 10-2014-0024657

(51) Int. Cl.
*A61B 8/14* (2006.01)
*A61B 8/00* (2006.01)
(Continued)

(52) U.S. Cl.
CPC .................. *A61B 8/56* (2013.01); *A61B 8/14* (2013.01); *A61B 8/4254* (2013.01);
(Continued)

(58) Field of Classification Search
CPC ....... G01S 7/003; G01S 7/52096; A61B 8/14; A61B 8/4254; A61B 8/4472; A61B 8/5207; A61B 8/56; Y02B 60/50
See application file for complete search history.

(56) References Cited

U.S. PATENT DOCUMENTS

| 6,142,946 A | 11/2000 | Hwang et al. |
| 6,592,521 B1 | 7/2003 | Urbano et al. |

(Continued)

FOREIGN PATENT DOCUMENTS

| CN | 101862204 A | 10/2010 |
| CN | 102824189 A | 12/2012 |

(Continued)

OTHER PUBLICATIONS

Extended European Search Report issued in Application No. 15150587.2 dated Aug. 6, 2015.

(Continued)

*Primary Examiner* — Angela M Hoffa
*Assistant Examiner* — Farouk A Bruce
(74) *Attorney, Agent, or Firm* — Morgan, Lewis & Bockius LLP

(57) ABSTRACT

Provided is a wireless probe including: an ultrasound reception/transmission module that receives a first power and scans a target object by transmitting ultrasound signals to the target object and receiving ultrasound echo signals reflected from the target object; a signal processing module that receives a second power, generates pulses for generating the ultrasound signals and generates ultrasound data by using the ultrasound echo signals; a wireless communication module that receives a third power and receives/transmits predetermined data from/to a medical device; a controller that controls supply of at least one of the first power, the second power, and the third power based on an operation state of the (Continued)

wireless probe; and a power unit that supplies or blocks the at least one of the first power, the second power, and the third power according to control of the controller. Each component included in the wireless probe may reduce power consumed by the wireless probe.

24 Claims, 10 Drawing Sheets

(51) Int. Cl.
  *G01S 7/52*     (2006.01)
  *A61B 8/08*     (2006.01)
  *G01S 7/00*     (2006.01)

(52) U.S. Cl.
  CPC .......... *A61B 8/4472* (2013.01); *A61B 8/5207* (2013.01); *G01S 7/52096* (2013.01); *G01S 7/003* (2013.01)

(56) References Cited

U.S. PATENT DOCUMENTS

| | | | |
|---|---|---|---|
| 6,752,761 B2 | 6/2004 | Amemiya | |
| 2006/0017014 A1 | 1/2006 | Shinada et al. | |
| 2007/0066978 A1* | 3/2007 | Schafer | A61B 5/02007 606/128 |
| 2008/0112265 A1 | 5/2008 | Urbano et al. | |
| 2008/0114249 A1* | 5/2008 | Randall | A61B 8/4472 600/447 |
| 2009/0150692 A1 | 6/2009 | Poland | |
| 2010/0262012 A1 | 10/2010 | Wu | |
| 2010/0277305 A1* | 11/2010 | Garner | A61B 8/00 340/539.1 |
| 2012/0197124 A1* | 8/2012 | Nakamura | A61B 8/42 600/443 |
| 2012/0226160 A1 | 9/2012 | Kudoh | |
| 2012/0323121 A1 | 12/2012 | Miller | |
| 2013/0053697 A1 | 2/2013 | Holl et al. | |
| 2014/0088425 A1 | 3/2014 | Tang et al. | |

FOREIGN PATENT DOCUMENTS

| | | | |
|---|---|---|---|
| CN | 102949209 A | 3/2013 | |
| JP | 11-108864 A | 4/1999 | |
| JP | 2006-020667 A | 1/2006 | |
| KR | 2001-0024871 A | 3/2001 | |
| KR | 2002-0079454 A | 10/2002 | |
| KR | 2004-0034797 A | 4/2004 | |
| KR | 10-2009-0078619 A | 7/2009 | |
| KR | 2012-0095185 A | 8/2012 | |
| WO | 2009/065167 A1 | 5/2009 | |
| WO | WO 2009/065167 A1 * | 5/2009 | ............... A61B 8/00 |
| WO | WO-2009065167 A1 * | 5/2009 | ............... A61B 8/00 |

OTHER PUBLICATIONS

Office Action issued in corresponding Chinese Patent Application No. 201510091613.5 dated Oct. 10, 2018.

* cited by examiner

WIRELESS PROBE AND METHOD FOR POWER CONTROLLING OF WIRELESS PROBE

RELATED APPLICATIONS

This application claims the benefit of Korean Patent Application No. 10-2014-0024657, filed on Feb. 28, 2014, in the Korean Intellectual Property Office, the disclosures of which are incorporated herein in its entirety by reference.

BACKGROUND

1. Field

One or more embodiments of the present invention relate to a wireless probe and a method of controlling power of the wireless probe, and more particularly, to a wireless probe that may reduce power consumption and a method of controlling power of the wireless probe.

2. Description of the Related Art

An ultrasound diagnosis device irradiates ultrasound signals generated by transducers of a probe to a target object and receives echo signals reflected from the target object, thereby obtaining images of the interior of the target object. Particularly, an ultrasound diagnosis device may be used for medical purposes including observation of the interior of a target object, detection of foreign substances, diagnosis of damage, etc. In comparison with other diagnosis devices using x-rays, the ultrasound diagnosis device has high stability, is capable of displaying images in real-time, and there is no possibility of radiation exposure, thus being highly safe. Therefore, the ultrasound diagnosis device is widely used together with other types of imaging diagnosis devices.

Regarding the ultrasound diagnosis device, a main body of the ultrasound diagnosis device that allows a user to manipulate a probe without a spatial limitation and a wireless probe that is connected via a wireless network have been developed. The wireless probe does not have separate power lines and is powered by internal batteries. In particular, a wireless probe that is wirelessly connected to a main body of an ultrasound diagnosis device for an ultrasound diagnosis or a wireless probe included in a portable ultrasound diagnosis device having a portable size has been developed.

The wireless probe is powered by internal batteries, and thus power consumption needs to be minimized. Therefore, there is need to provide a wireless probe capable of minimizing power consumption and a method of controlling power of the wireless probe without any user inconvenience when the user performs ultrasound scanning.

SUMMARY

One or more embodiments of the present invention include a wireless probe capable of minimizing power consumption and a method of controlling power of the wireless probe.

Additional aspects will be set forth in part in the description which follows and, in part, will be apparent from the description, or may be learned by practice of the presented embodiments.

According to one or more embodiments of the present invention, a wireless probe includes: an ultrasound reception/transmission module that receives a first power and scans a target object by transmitting ultrasound signals to the target object and receiving ultrasound echo signals reflected from the target object; a signal processing module that receives a second power, generates pulses for generating the ultrasound signals and generates ultrasound data by using the ultrasound echo signals; a wireless communication module that receives a third power and receives/transmits predetermined data from/to a medical device; a controller that controls supply of at least one of the first power, the second power, and the third power based on an operation state of the wireless probe; and a power unit that supplies or blocks the at least one of the first power, the second power, and the third power according to control of the controller.

The controller may separately supply or block the at least one of the first power, the second power, and the third power based on the operation state of the wireless probe.

The controller may supply the first power, the second power, and the third power when the wireless probe performs scanning.

The controller may block the first power and may supply at least one of the second power and the third power when the wireless probe finishes performing scanning.

The controller may block the first power and may supply the second power and the third power when the wireless probe finishes performing the scanning and does not finish processing the ultrasound data.

The controller may block the first power and the second power and may supply the third power when the wireless probe finishes performing the scanning and processing ultrasound data.

The controller may block the first power and the second power and may supply the third power when manipulation of the wireless probe is not detected for a first time.

The controller may block the first power, the second power, and the third power when manipulation of the wireless probe is not detected for a second time.

The controller may block the first power, the second power, and the third power and may allow the wireless probe to be in a standby state when the manipulation of the wireless probe is not detected for the second time.

The controller may block the first power, the second power, and the third power and may turn off the wireless probe when manipulation of the wireless probe is not detected for a third time.

The wireless probe may further include a detector that detects whether a user manipulates the wireless probe.

The detector may include at least one of a gyro sensor, a position sensor, an acceleration sensor, a temperature sensor, and a pressure sensor.

The detector may generate a first even signal having a first signal level and may transmit the generated first event signal to the controller when it is determined that the wireless probe is scanning the target object based on detection results of the detector.

The ultrasound reception/transmission module may include: at least one transducer that generates the ultrasound signals when a predetermined voltage is applied; an ultrasound generation unit that transmits driving signals for generating the ultrasound signals to the at least one transducer; and an ultrasound reception unit that receives and focuses the ultrasound echo signals transmitted by the at least one transducer.

The first power may include at least one of power for supplying the predetermined voltage, ultrasound transmission beam-forming power for generating transmit-focused ultrasound signals, and sound reception beam-forming power for generating the ultrasound echo signals that are received and focused.

The second power may include at least one of power for generating the pulses, and power used to process at least one of the ultrasound data and an ultrasound image corresponding to the ultrasound data.

The third power may include at least one of pairing power used to link the wireless probe with the medical device, and power used to adjust a sensitivity of signals for receiving/transmitting the predetermined data.

The controller may generate information about a power supply state of at least one of the first power, the second power, and the third power and may transmit the information to the medical device.

The wireless probe may further include a display that displays a user interface screen indicating power supply states of the first power, the second power, and the third power.

The wireless probe may further include a display that displays a user interface screen used to set a power supply of at least one of the first power, the second power, and the third power.

The wireless probe may further include an alarm unit that outputs alarm signals for allowing a user to recognize a change in a power supply state of at least one of the first power, the second power, and the third power when the power supply state of the at least one of the first power, the second power, and the third power is changed.

The alarm unit may include at least one of a speaker, a lamp, a vibrator, and a display.

The controller may output a user interface screen including a security setting menu for allowing manipulation of the wireless probe when the wireless probe is turned on.

The power unit may charge power and may include a battery that supplies at least one of the first power, the second power, and the third power by using the charged power.

The power unit may receive wireless power from the outside and may supply at least one of the first power, the second power, and the third power by using the received wireless power.

According to one or more embodiments of the present invention, a method of controlling power of a wireless probe, includes: recognizing an operation state of the wireless probe; and controlling at least one of a first power supplied to an ultrasound reception/transmission module, which scans a target object by transmitting ultrasound signals to the target object and receiving ultrasound echo signals reflected from the target object, a second power supplied to a signal processing module, which generates pulses for generating the ultrasound signals and generates ultrasound data by using the ultrasound echo signals, and a third power supplied to a wireless communication module, which receives/transmits predetermined data from/to a medical device based on the operation state of the wireless probe.

The controlling of the at least one of the first power, the second power, and the third power comprises selectively supplying or blocking the first power, the second power, the third power based on the operation state of the wireless probe.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
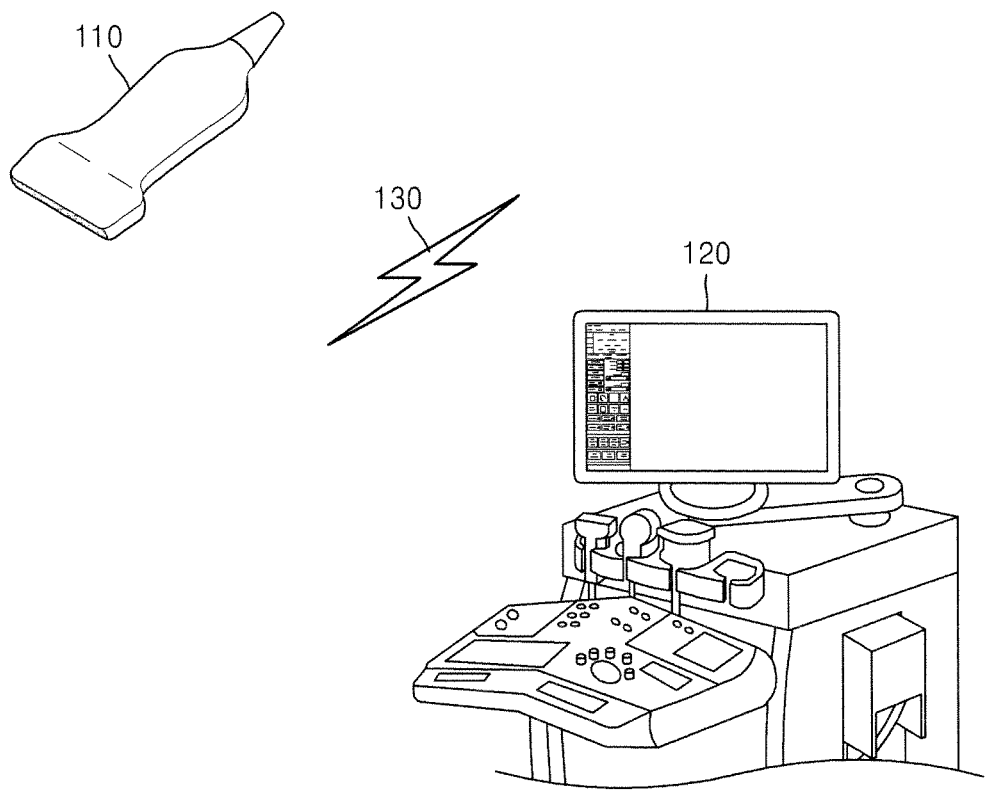
FIG. 1 is a view of a wireless probe and a main body forming an ultrasound diagnosis device.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of", when preceding a list of elements, modify the entire list of elements and do not modify the individual elements of the list.

Throughout the specification, when a portion is "connected" to another portion, the portion may be "directly connected" to the other portion, and also the portion may be "electrically connected" to the other portion by interposing a device therebetween. Also, when a portion "includes" an element, another element may be further included, rather than excluding the existence of the other element, unless otherwise described. Terms such as " . . . unit", " . . . module", or the like refer to units that perform at least one function or operation, and the units may be implemented as hardware or software or as a combination of hardware and software.

Throughout the specification, an "ultrasonic image" refers to an image of an object that is obtained using an ultrasonic wave. Furthermore, in the present specification, an "object" may include a person or an animal, or a part of a person or an animal. For example, the object may include the liver, the heart, the womb, the brain, a breast, the abdomen, or a blood vessel. Furthermore, the "object" may include a phantom. The phantom means a material having a volume that is approximately the intensity and effective atomic number of a living thing, and may include a sphere phantom having a property similar to a human body.

Furthermore, in the present specification, a "user" refers to a medical professional, such as a doctor, a nurse, a medical laboratory technologist, and an engineer who repairs a medical apparatus, but the user is not limited thereto.

FIG. 1 is a view of a wireless probe 110 and a main body 120 forming an ultrasound diagnosis device.

Referring to FIG. 1, the ultrasound diagnosis device includes the wireless probe 110 and the main body 120.

The wireless probe 110 is wirelessly connected to the main body 120 via a wireless network 130 and obtains ultrasound data by transmitting ultrasound signals to a target object and receiving echo signals reflected from the target object. An ultrasound image is generated by using the obtained ultrasound data, and the generated ultrasound image may be transmitted to the main body 120. Alternatively, the wireless probe 110 transmits the obtained ultrasound data to the main body 120, and the main body 120 may generate an ultrasound image by using the transmitted ultrasound data.

The main body 120 receives/transmits predetermined data from/to the wireless probe 110, and an ultrasound image having various modes may be generated by using the ultrasound data transmitted by the wireless probe 110. In addition, operations of the wireless probe 110 may be controlled based on user inputs. The main body 120 may be implemented as a cart-type main body or a mobile main body. Examples of the main body 120 are a cart-type ultrasound system, a picture archiving and communication system (PACS) viewer, a smartphone, a laptop computer, a personal digital assistant (PDA), a tablet PC, or the like, but are not limited thereto.

While a user scans a certain body part of a patient who is the target object by using the wireless probe 110, the wireless probe 110 and the main body 120 are in a state in which the wireless probe 110 continuously receives/transmits data from/to the main body 120 via the wireless network 130.

The wireless probe 110 may receive/transmit the data from/to the main body 120. However, the wireless probe 110 may not receive power from the main body 120 and is powered by batteries (not shown) that are installed in the wireless probe 110.

The batteries (not shown) of the wireless probe 110 have a limited power capacity. Therefore, when the user does not save the power of the batteries (not shown), the user may not use the wireless probe 110 due to discharge of the batteries (not shown) regardless of a user's intention.

The wireless probe 110 may minimize power consumption by effectively controlling the power consumed by the wireless probe 110. Hereinafter, the wireless probe 110 will be described in detail with reference to FIGS. 2 through 9.

Figure 2:
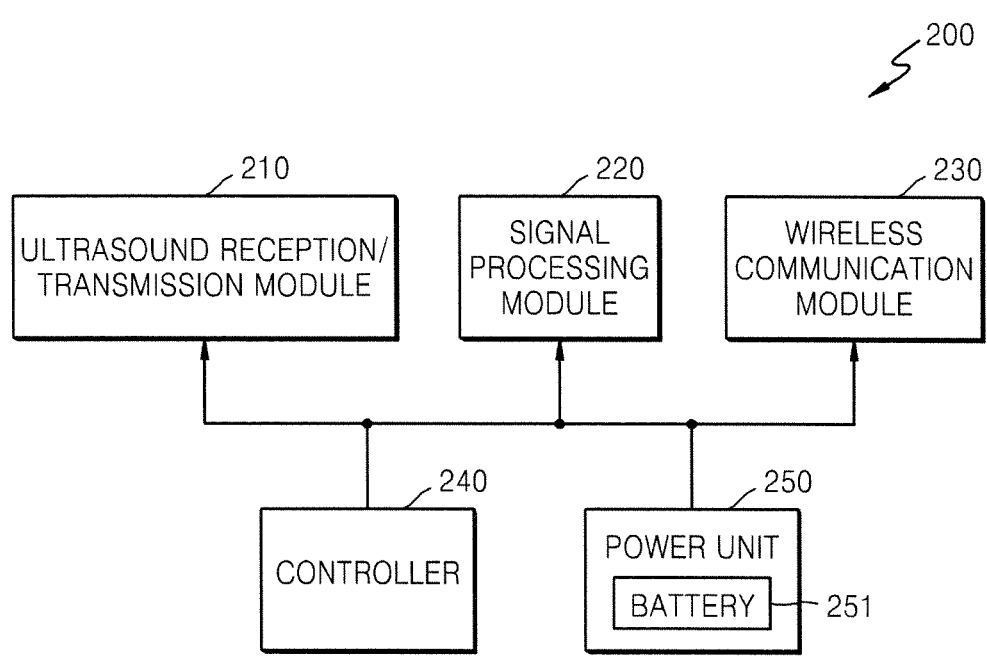
FIG. 2 is a block diagram of a wireless probe according to an embodiment of the present invention.

FIG. 2 is a block diagram of a wireless probe 200 according to an embodiment of the present invention.

The wireless probe 200 is an ultrasound probe that scans a target object and performs ultrasound scanning by receiving power from batteries included in the wireless probe 200 instead of from an external power source transmitted via power lines. In addition, the wireless probe 200 may be a probe that is wirelessly connected to a main body as illustrated in FIG. 1. Alternatively, the wireless probe 200 may be a portable ultrasound diagnosis device such as a smart device capable of performing ultrasound scanning since the wireless probe 200 includes transducers.

Referring to FIG. 2, the wireless probe 200 includes an ultrasound reception/transmission module 210, a signal processing module 220, a wireless communication module 230, a controller 240, and a power unit 250.

The ultrasound reception/transmission module 210 receives a first power and scans the target object by transmitting ultrasound signals and receiving ultrasound echo signals reflected from the target object. In particular, the ultrasound reception/transmission module 210 includes transducers (not shown) and performs ultrasound scanning for the target object by using the transducers. The first power is supply power corresponding to the power consumed by the ultrasound reception/transmission module 210. That is, the first power is the power that the power unit 250 supplies to the ultrasound reception/transmission module 210 when the ultrasound reception/transmission module 210 receives power necessary to perform the ultrasound scanning from the power unit 250. In particular, the ultrasound reception/transmission module 210 may apply a high voltage that is an analog voltage to the transducers, and the first power may include the analog voltage.

The signal processing module 220 receiving a second power generates pulses for generating the ultrasound signals and then generates ultrasound data by using the ultrasound echo signals. In particular, the signal processing module 220 generates and controls the pulses for generating the ultrasound signals, wherein the pulses are generated in the ultrasound reception/transmission module 210. Also, the signal processing module 220 processes the ultrasound echo signals received from the ultrasound reception/transmission module 210 and may generate ultrasound data or an ultrasound image by using the ultrasound data. The second power is supply power corresponding to the power consumed by the signal processing module 220. That is, the second power is the power that the power unit 250 supplies to the signal processing module 220 when the signal processing module 220 receives the power necessary to perform ultrasound scanning from the power unit 250.

In particular, the signal processing module 220 requires a digital voltage having a predetermined frequency, a predetermined clock speed, or a predetermined sampling rate to generate and controls the pulses, and the second power may include the power for generating the digital voltage.

The wireless communication module 230 receives a third power and receives/transmits data from/to a medical device (not shown). The medical device may be any kind of electronic devices that are linked to the wireless probe 200 via a wireless network. In particular, the medical device may correspond to the main body 120 of FIG. 1 and may be a cart-type ultrasound system, a PACS viewer, a smartphone, a laptop computer, a PDA, a tablet PC, or the like. Furthermore, the medical device (not shown) that receives/transmits the data from/to the wireless communication module 230 may be a server or a medical device in a hospital or may be a mobile terminal of a patient. In addition, the medical device may be another type of medical imaging system such as a system applying computed tomography (CT), magnetic resonance imaging (MRI), or x-rays.

For example, the wireless communication module 230 transmits the ultrasound data or the ultrasound image generated in the signal processing module 220 to the medical device, and the medical device may generate and display the ultrasound image by using the transmitted ultrasound data.

The controller 240 may selectively supply or block the first power, the second power, and the third power based on an operation state of the wireless probe 200.

In particular, the controller 240 may control the supply of at least one of the first power, the second power, and the third power based on event signals for controlling the power supply. The event signals are control signals for selectively supplying or blocking at least one of the first power, the second power, and the third power. The event signals are signals that indicate the operation state of the wireless probe 200 and may be signals that indicate an operation state of at least one of the ultrasound reception/transmission module 210, the signal processing module 220, and the wireless communication module 230. The event signals will be described in detail with reference to FIGS. 4A through 4C.

The power unit 250 supplies at least one of the first power, the second power, and the third power according to the control of the controller 240.

The power unit 250 charges the power of the wireless probe 200 and may include a battery 251 that supplies at least one of the first power, the second power, and the third power by using the charged power. The battery 251 charges the power and may provide the charged power to each component included in the wireless probe 200.

For example, the battery 251 is a rechargeable battery and may be recharged by using the power supplied via power lines when the battery 251 is discharged. In addition, the battery 251 may be recharged by wireless power from the outside.

Also, the power unit 250 may receive the wireless power from the outside. The power unit 250 may provide at least one of the first power, the second power, and the third power to the wireless probe 200 by using the wireless power from the outside. In detail, the power unit 250 receives wireless power signals from the outside, for example, the main body 120, etc., and stores power generated by converting the received wireless power signals in order to use the generated power.

In particular, a wireless power supply method may be an electromagnetic induction method based on electromagnetic induction that occurs due to the wireless power signals, a resonance method based on electromagnetic resonance that occurs due to wireless power signals having a certain frequency, a radiation method based on electromagnetic wave emission (e.g. a non-radiative wireless energy transmission method), a wireless power transmission method using ultrasound (refer to an U.S. Pat. No. 6,798,716 by Charych Arthur with regard to energy transmission using ultrasound), or the like.

The power unit 250 may receive the power by using at least one of the above-described wireless power transmission methods. The power unit 250 receives the wireless power from the outside and may convert the received wireless power into power that is appropriate to be supplied to each component included in the wireless probe 200. That is, the power unit 250 may convert the received wireless power into power that is smaller than a rated voltage and a rated current. For example, the power unit 250 includes a switched-mode power supply (SMPS) (not shown), a voltage booster, and/or a voltage drop device (not shown) and may convert the wireless power by using the above-listed devices. The battery 251 included in the power unit 250 may be charged by the received wireless power. The battery 251 may provide the power to each component included in the wireless probe 200 by using the power charged by using the wireless power.

Since the ultrasound reception/transmission module 210, the signal processing module 220, and the wireless communication module 230 included in the wireless probe 200 may independently operate, the power consumed by the wireless probe 200 is classified into three types: the first power supplied to the ultrasound reception/transmission module 210, and second power supplied to the signal processing module 220, and the third power supplied to the wireless communication module 230. Moreover, the aforementioned types of power are selectively supplied or blocked.

That is, the ultrasound reception/transmission module 210, the signal processing module 220, and the wireless communication module 230 included in the wireless probe 200 may independently operate. Although the power supplied to any one of the ultrasound reception/transmission module 210, the signal processing module 220, and the wireless communication module 230 is blocked according to operation states, the others may properly operate. Therefore, the power supplied to the ultrasound reception/transmission module 210, the signal processing module 220, and the wireless communication module 230 is separately supplied or blocked in consideration of the operation state of the wireless probe 200. Accordingly, the wireless probe 200 may minimize power consumption. In addition, although the power consumption is minimized, operations of the wireless probe 200 are not affected, and the wireless probe 200 may be used without limitation.

Figure 3:
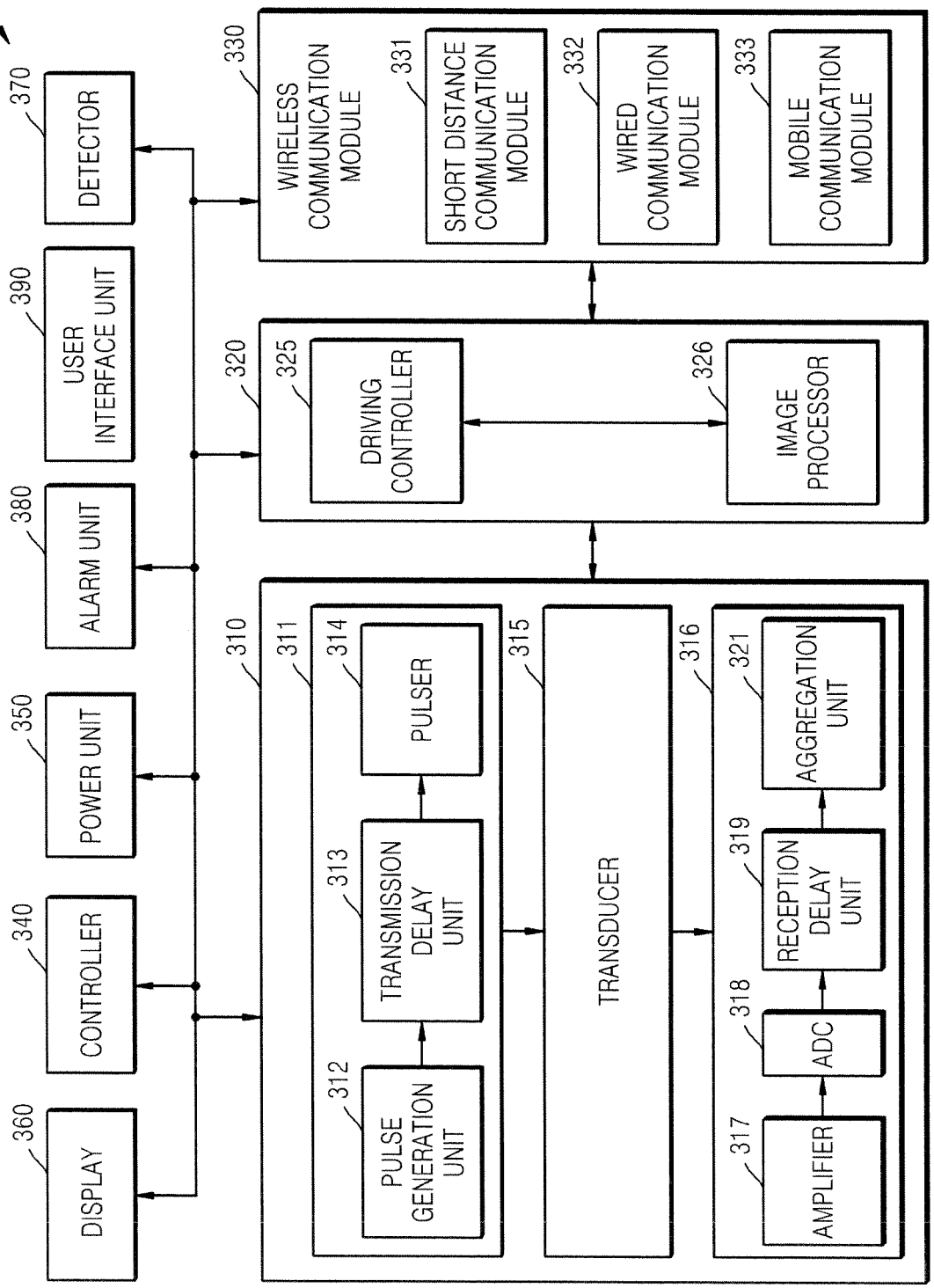
FIG. 3 is a block diagram of a wireless probe according to another embodiment of the present invention.

FIG. 3 is a block diagram of a wireless probe 300 according to another embodiment of the present invention.

Referring to FIG. 3, the wireless probe 300 partly corresponds to the wireless probes 110 and 200. In particular, an ultrasound reception/transmission module 310, a signal processing module 320, a wireless communication module 330, a controller 340, and a power unit 350 included in the wireless probe 300 respectively correspond to the ultrasound reception/transmission module 210, the signal processing module 220, the wireless communication module 230, the controller 240, and the power unit 250 included in the wireless probe 200, and thus descriptions thereof are not repeatedly provided. The wireless probe 300 of FIG. 3 may further include at least one of a display 360, a detector 370, an alarm unit 380, and a user interface unit 390, in comparison with the wireless probe 200 of FIG. 2.

The ultrasound reception/transmission module 310 receives the first power and scans the target object by transmitting ultrasound signals to a target object and receiving ultrasound echo signals reflected from the target object. The ultrasound reception/transmission module 310 may include an ultrasound transmission unit 311, a transducer 315, and an ultrasound reception unit 316. The transducer 315 is an ultrasound scanning device, and the ultrasound reception/transmission module 310 includes at least one transducer. However, the at least one transducer is referred to as the 'transducer 315' in FIG. 3 for convenience of explanation.

The ultrasound transmission unit 311 transmits driving signals to the transducer 315 in order to allow the transducer 315 to generate transmit-focused ultrasound signals. In detail, the ultrasound transmission unit 311 may include a pulse generation unit 312, a transmission delay unit 313, and a pulser 314.

The pulse generation unit 312 generates pulses for generating transmission ultrasound according to a pulse repetition frequency (PRF).

The transmission delay unit 313 applies a delay time for determining transmission directionality to the pulses. The pulses, to which the delay time is applied, correspond to piezoelectric vibrators (not shown) included in the transducer 315, respectively. The piezoelectric vibrators may be referred to as piezoelectric devices. In particular, the transmission delay unit 313 transmits and focuses transmit ultrasound and then generates pulses for generating the transmit-focused ultrasound signals.

The pulser 314 applies driving signals (or driving pulses), which are times corresponding to the pulses, to which the delay time is applied.

The transducer 315 vibrates according to the pulses that are electrical signals applied to the transducer 315 and generates ultrasound that is sound energy in the form of waves to transmit the generated ultrasound to the target object. Then, the transducer 315 receives ultrasound echo signals that are ultrasound signals reflected from the target object.

The transducer 315 may include an acoustic lens (not shown), a piezoelectric device (not shown), a matching layer (not shown), and an ultrasound absorption layer (not shown).

The piezoelectric device is formed of a piezoelectric effect element that converts electrical signals into sound signals and vice versa. The piezoelectric effect element may be piezoelectric ceramic, a single crystal, or a compound piezoelectric material in which the previous materials are combined with polymers. When the pulses that are electrical signals generated by the pulser 314 are applied to the piezoelectric device, ultrasound signals may be generated in the piezoelectric device. The pulses applied to the piezoelectric device are voltage signals and have certain voltage values.

The matching layer (not shown) is disposed at a front portion of the piezoelectric device. The matching layer changes acoustic impedance of ultrasound generated in the piezoelectric device by stages and makes the acoustic impedance of the ultrasound close to acoustic impedance of the target object. The front portion of the piezoelectric device may be a portion that is the closest to the target object from among surfaces of the piezoelectric device while the ultrasound is applied to the target object. A rear portion of the piezoelectric device may be a portion opposite to the front portion thereof. The matching layer may be referred to as an acoustic matching layer.

The ultrasound absorption layer supports the piezoelectric device at the rear surface of the piezoelectric device and may absorb the ultrasound which is transmitted to the rear surface of the piezoelectric device and is not directly used for an examination or a diagnosis of the target object. Also, electrodes that apply a predetermined voltage to the piezoelectric device may be formed in the ultrasound absorption layer.

The acoustic lens is disposed at a front portion of the transducer 315 and focuses the ultrasound generated in the piezoelectric device. The acoustic lens may be formed of materials such as silicone rubber having acoustic impedance close to that of the target object.

The ultrasound reception unit 316 receives and focuses the ultrasound echo signals that are transmitted by the transducer 315 and generates the received and focused ultrasound echo signals. In detail, the ultrasound reception unit 316 receives and focuses the ultrasound echo signals transmitted by the transducer 315 and generates ultrasound data.

The ultrasound reception unit 316 may include an amplifier 317, an analog digital converter (ADC) 318, a reception delay unit 319, and an aggregation unit 321.

The amplifier 317 amplifies the ultrasound echo signals in channels, and the ADC 318 analog-digital converts the amplified ultrasound echo signals. The reception delay unit 319 applies a delay time for determining reception directionality to the digitally converted ultrasound echo signals. In the present embodiment, each of the channels means a channel for each device of the transducer 315.

The aggregation unit 321 generates the ultrasound data by aggregating the ultrasound echo signals processed by the reception delay unit 319. The ultrasound reception unit 316 may not include the amplifier 317 according to an implementation type thereof. That is, if the received ultrasound echo signals do not need to be amplified because a reception sensitivity of the ultrasound echo signals of the transducer 315 is improved or the number of bits processed in the ADC 318 is increased, the amplifier 317 may not be included in the ultrasound reception unit 316.

In particular, the first power supplied to the ultrasound reception/transmission module 310 may include at least one of power corresponding to a voltage applied to the transducer 315 to generate the ultrasound signals, ultrasound transmission beam-forming power for generating the transmit-focused ultrasound signals, and ultrasound reception beam-forming power for generating the received and focused ultrasound echo signals.

In particular, the sound beam-forming power is power required by the ultrasound transmission unit 311 and means power necessary to focus a beam of the transmitted ultrasound signals by applying the delay time to the ultrasound signals transmitted to the target object. The sound reception beam-forming power is power required by the ultrasound reception unit 316 and means power necessary to control dynamic focusing of the ultrasound signals reflected from the target object.

A voltage that the transducer 315 needs to receive to generate the ultrasound signals (hereinafter, referred to as 'transducer supply high voltage') is a voltage applied to the piezoelectric device and may be a high voltage in a range from about −100V to about +100V. Also, in the case of a two-dimensional (2D) or three-dimensional (3D) wireless probe, since the 2D or 3D wireless probe may include hundreds or thousands of channels, an application specific integrated circuit (ASIC) may be used to group the channels and control the grouped channels by stages. When the ASIC is included in the ultrasound transmission unit 311, the power consumed by the ultrasound reception/transmission module 310 may further include an operation voltage of the ASIC, for example, a voltage in a range from about −40V to about +40V.

Also, the sound transmission beam-forming power may include operation voltages of the pulse generation unit 312, the transmission delay unit 313, and the pulser 314. The sound reception beam-forming power may include operation voltages of the amplifier 317, the ADC 318, the reception delay unit 319, and the aggregation unit 321.

Therefore, the first power is power corresponding to the power necessary for operations of the ultrasound reception/transmission module 310 as described above.

The signal processing module 320 may include a driving controller 325 and an image processor 326.

The driving controller 325 may generate control signals for controlling an operation for generating the ultrasound signals. A delay time of the ultrasound signals, which are transmitted according to a depth and a focal point of the ultrasound signals, needs to be differently set in order to focus a beam to the target object. The driving controller 325 may generate control signals for setting the delay time. In addition, the pulses generated by the pulser 314 have a predetermined frequency, and, in this case, the driving controller 325 needs to generate sampling signals corresponding to the frequency to be applied by the pulser 314. Accordingly, the driving controller 325 may generate the sampling signals. The driving controller 325 needs to receive a driving voltage necessary to generate the control signals and the sampling signals for setting the delay time.

The image processor 326 receives the ultrasound data transmitted by the ultrasound reception unit 316 and processes the received ultrasound data. The image processor 326 may perform signal processing such as noise removal and data conversion and may generate ultrasound imaging signals by scanning and converting the ultrasound data.

Furthermore, the image processor 326 may directly generate an ultrasound image indicating the object. In detail, the image processor 326 may generate images in an amplitude (A) mode, a brightness (B) mode, a motion (M) mode and a Doppler mode by using the ultrasound data transmitted by the ultrasound reception unit 316.

The second power supplied to the signal processing module 320 includes operation voltages for operating the driving controller 325 and the image processor 326. The second power may include at least one of power used to generate the pulses in the pulse generation unit 312 and power used to generate at least one of the ultrasound data and the ultrasound image corresponding to the ultrasound data. For example, the second power may include at least one of a voltage necessary for the driving controller 325 to generate the control signals for setting the delay time, a voltage necessary to generate the sampling signals supplied to the pulser 314, and a driving voltage necessary for the image processor 326 to perform ultrasound data processing and ultrasound image processing.

The wireless communication module 330 may include at least one communication module for wirelessly communicating with a medical device. The wireless communication module 330 may include at least one of a short distance communication module 331, a wired communication module 332, and a mobile communication module 333.

The short distance communication module 331 is a module for short distance communication within a predetermined distance. Short distance communication technology may be technology with regard to wireless LAN, Wi-Fi, Bluetooth, ZigBee, Wi-Fi Direct (WFD), ultra wideband (UWB), infrared data association (IrDA), Bluetooth low energy (BLE), near field communication (NFC), or the like, but is not limited thereto.

The wired communication module 332 is a module for communication using electrical signals or optical signals, and wired communication technology may include technology using pair cables, coaxial cables, optical fiber cables, Ethernet cables, etc.

The mobile communication module 333 receives/transmits wireless signals from/to at least one of a base station, an external terminal, and a server via a mobile communication network. The wireless signals may include various types of data according to reception/transmission of voice call signals, video call signals, or a text/multimedia message.

The wireless communication module 330 may receive/transmit predetermined data from/to an external medical device (not shown) via various communication modules included in the wireless communication module 330.

The third power is power necessary to operate the wireless communication module 330 and may include at least one of pairing power used to link the wireless communication module 330 with the external medical device, and operation power of a sensitivity control circuit for controlling the sensitivity of signals used to receive/transmit the predetermined data. The wireless probe 300 needs to be interconnected with the external medical device via a wireless network in order to receive/transmit the predetermined data from/to the external medical device. The wireless probe 300 and the external medical device need to be synchronized to continuously and periodically communicate with each other. Therefore, the third power may include pairing power necessary to maintain a connection between the wireless probe 300 and the external medical device, power necessary to receive/transmit the predetermined data from/to the external medical device, and power for controlling the signal sensitivity of the received/transmitted data.

The controller 340 controls the supply of at least one of the first power, the second power, and the third power based on an operation state of the wireless probe 300. In particular, the controller 340 may separately supply or block the first power, the second power, and the third power based on the operation state of the wireless probe 300. The controller 340 may control the supply of at least one of the first power, the second power, and the third power according to event signals indicating the operation state of the wireless probe 300.

The display 360 displays a predetermined screen according to the control of the controller 340. The display 360 includes a display panel (not shown) and may display a user interface screen, a medical image screen, or the like on the display panel.

The detector 370 may detect the operation state of the wireless probe 300. The detector 370 may determine whether a user manipulates the wireless probe 300. The detector 370 may determine whether the user performs scanning by using the wireless probe 300.

The alarm unit 380 may output alarm signals for allowing the user to recognize a change of a power supply state when a power supply state of at least one of the first power, the second power and the third power is changed. The alarm unit 380 may include at least one of a speaker, a lamp, a vibrator, and a display.

The user interface unit 390 may generate and output a user interface screen for receiving a predetermined command or data from the user. The user interface unit 390 receives the predetermined command or data from the user through the user interface screen. The user may recognize predetermined information after watching the user interface screen displayed via the display 360 and may input the predetermined command or data via the user interface unit 390.

For example, the user interface unit 390 may include a mouse, a keyboard, and input devices including hard keys for inputting the predetermined data. For example, the user manipulates at least one of the mouse, the keyboard, and other input devices included in the user interface unit 390 and may input the predetermined command or data.

As another example, the user interface unit 390 may be a touch pad. In particular, the user interface unit 390 may include a touch panel combined with the display panel (not shown) included in the display 360. In this case, the user interface screen is output on the display panel. Also, when the predetermined command is input via the user interface screen, the touch pad detects the input of the command and transmits the detected command to the controller 340. Then, the controller 340 analyzes the detected command and may recognize and execute the predetermined command input by the user.

In a case where the user interface unit 390 is a touch pad, when the user touches a certain location of the user interface screen, the user interface unit 390 detects the touched location of the user interface screen. Then, the user interface unit 390 may transmit information about the detected location to the controller 340. Then, the controller 340 recognizes a request or a command of the user, which corresponds to a menu displayed on the detected location, and may perform the recognized request or command.

If the target object is being scanned, the controller 340 may provide the first power, the second power, and the third power.

When the scanning of the target object is finished, the controller 340 blocks the first power and may provide at least one of the second power and the third power. When the scanning is finished but the processing of the ultrasound data is not finished, the controller 340 blocks the first power and may provide the second power and the third power. When the scanning of the target object and the processing of the ultrasound data are finished, the controller 340 blocks the first power and the second power and may provide the third power.

In addition, when the user does not manipulate the wireless probe 300 for a first time, the controller 340 blocks the first power and the second power and may provide the third power. The first time is a time necessary to obtain and process the ultrasound data and may vary depending on a specification of a product, for example, a data processing speed. In particular, the first time may be a time required to finish generation of the ultrasound data to be transmitted to an external medical device after the target object is completely scanned by the ultrasound reception/transmission module 310, and the ultrasound data, which is obtained after the scanning of the target object is finished, is processed in the signal processing module 320. Moreover, the user may autonomously set the first time.

When the first time passes after the user does not manipulate the wireless probe 300, the controller 340 supplies only the third power including the pairing power for the connection with the external medical device and may block the first power and the second power.

In addition, when the user does not manipulate the wireless probe 300 for a second time that is greater than the first time, the controller 340 may block the first, second, and third power. The second time may be set by considering a time required to completely transmit the ultrasound data or the ultrasound image, which is generated in the signal processing module 320, from the wireless communication module 330 to the external medical device. The user may autonomously set the second time. When the first, second, and third power is blocked, the wireless probe 300 is in a standby state.

When the user does not manipulate the wireless probe 300 for a third time that is greater than the second time, the controller 340 completely turns off the wireless probe 300 and may not generate standby power required to maintain the wireless probe 300 in a standby state.

Furthermore, the controller 340 may store a current state and environment settings of the wireless probe 300 before the wireless probe 300 is completely turned off. Accordingly, when the user turns on the wireless probe 300 to operate, the controller 340 may reboot the wireless probe 300 by using the stored state and environment settings. Hereinafter, a state in which the wireless probe 300 is completely turned off and the standby power is not consumed is referred to as a 'power-off state', and a state in which the wireless probe 300 receives power in the power-off state and operates is referred to as a 'power-on state'.

As described above, power that is necessary in a current operation state of the wireless probe 300 may be selectively supplied by selectively supplying or blocking voltages that are respectively applied to the ultrasound reception/transmission module 310, the signal processing module 320, and the wireless communication module 330 based on the operation state of the wireless probe 300. Accordingly, the power consumption of the wireless probe 300 may be reduced by effectively blocking unnecessary power in consideration of the current operation state of the wireless probe 300.

In detail, the operation state of the wireless probe 300 may be determined according to a detection result of the detector 370, and the controller 340 may control the supply of the first power, the second power, and the third power according to the detection result of the detector 370.

The detector 370 may include at least one of a gyro sensor, a position sensor, an acceleration sensor, a temperature sensor, and a touch sensor such as a pressure sensor. Operations of the detector 370 will be described in detail with reference to FIGS. 4A through 4C.

In addition, the controller 340 may decrease or increase a voltage level of at least one of the first power, the second power, and the third power according to the operation state of the wireless probe 300. For example, when the amount of power charged in the power unit 350 is decreased by a predetermined threshold value, a level of the high voltage included in the first power may be decreased by a predetermined offset value. For example, when the amount of the power charged in the power unit 350 is decreased by 30% or less, the controller 340 may control the high voltage, which will be supplied to the transducer 315, to be decreased from about 100 V to about 70 V. As described above, when the first power is decreased and then applied to the wireless probe 300, values of obtained ultrasound signals may be decreased. However, a maintaining time of the ultrasound scanning may be increased.

Figure 4A:
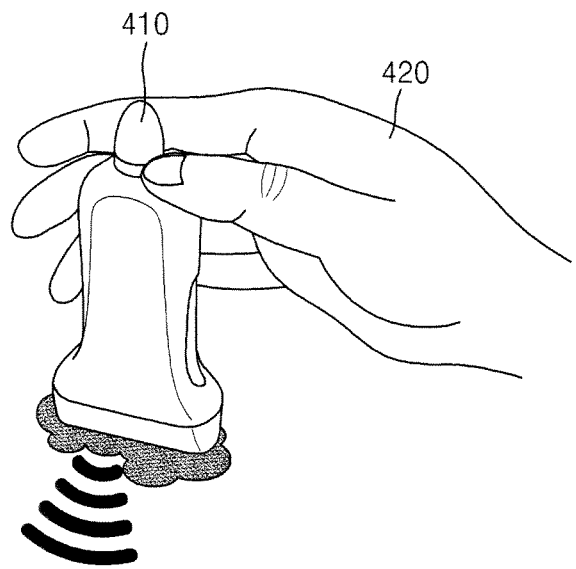
FIGS. 4A through 4C are views of operations of a wireless probe according to another embodiment of the present invention.
Figure 4B:
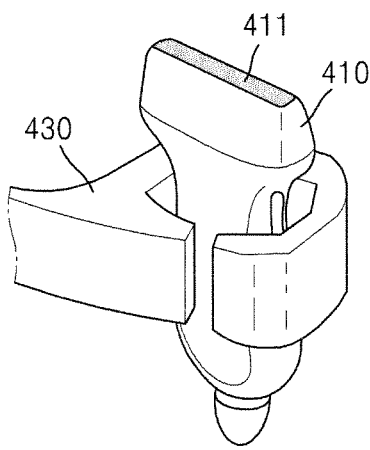
Figure 4C:
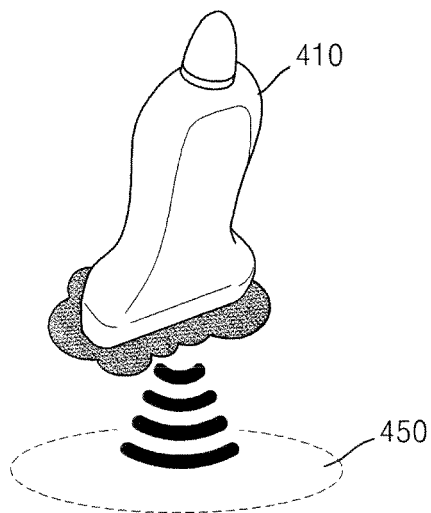

FIGS. 4A through 4C are views of operations of a wireless probe 410 according to another embodiment of the present invention. Referring to FIGS. 4A through 4C, the wireless probe 410 corresponds to the wireless probe 300, and the wireless probe 410 includes a detector (not shown) corresponding to the detector 370. The detector (not shown) included in the wireless probe 410 is described with reference to the detector 370.

Referring to FIG. 4A, the detector 370 may include at least one of a temperature sensor (not shown), and a touch sensor (not shown) such as a pressure sensor in order to determine whether a user 420 performs the scanning by using the wireless probe 410. For example, when the detector 370 includes the temperature sensor, the detector 370 detects a temperature of the user 420 when the user 420 contacts the wireless probe 410 and may determine that the user 420 manipulates the wireless probe 410.

In addition, when the detector 370 includes the touch sensor, the detector 370 detects touches by the user 420 and may determine that the user 420 manipulates the wireless probe 410.

Referring to FIG. 4B, the detector 370 may include at least one of a gyro sensor (not shown) and a position sensor (not shown). The gyro sensor detects whether pressure is applied in a direction of gravity, and the position sensor detects a position of the wireless probe 410.

In general, when the user 420 does not use the wireless probe 410, the user 420 places a transducer of the wireless probe 410 to face upwards on a supporter 430 in order to protect an acoustic lens 411 disposed on an outer surface of the transducer. When the user 420 scans the target object by using the wireless probe 410, the user 420 holds the wireless probe 410 backwards such that the acoustic lens 411 faces downwards. The gyro sensor or the position sensor may detect whether the acoustic lens 411 of the wireless probe 410 faces upwards or downwards as illustrated in FIG. 4B.

When the gyro sensor or the position sensor determines that the acoustic lens 411 faces upwards or is horizontally placed as illustrated in FIG. 4B, the gyro sensor or the position sensor may determine that the user 420 does not manipulate the wireless probe 410.

Referring to FIG. 4C, the detector 370 may include an acceleration sensor (not shown). When the user 420 contacts and moves the wireless probe 410 on the target object, the acceleration sensor detects movements on the target object and may determine that the user 420 manipulates the wireless probe 410. Also, when the acceleration sensor does not detect the movements on the target object, the acceleration sensor may determine that the user 420 manipulates the wireless probe 410.

The wireless probe 410 may not include the detector 370 and may determine whether the user performs the scanning of the target object by periodically transmitting the ultrasound signals. In general, when the user 420 scans the target object, the user 420 applies a gel for an ultrasound diagnosis on the acoustic lens 411 so as to improve the transmission of the ultrasound signals to the target object. In this case, types of the ultrasound echo signals received by the wireless probe 410 vary according to whether the gel is applied on the acoustic lens 411. Therefore, the controller 340 of the wireless probe 410 may determine whether the user 420 scans the target object by periodically transmitting the ultrasound signals to the target object and observing the types of the ultrasound echo signals received by the wireless probe 410.

As described above, an operation state of the wireless probe 410, in other words, whether the user 420 scans the target object, may be determined according to the detection result of the detector 370, and then the controller 340 may control power supply.

For example, when it is determined that the user 420 scans the target object by using the wireless probe 410 based on the detection result of the detector 370, the controller 340 may supply the first power, the second power, and the third power.

In particular, when it is determined that the user 420 scans the target object by using the wireless probe 410 based on the detection result of the detector 370, the detector 370 may output the event signals as first event signals. When it is determined that the user 420 scans the target object by using the wireless probe 410, the detector 370 may output the event signals as second event signals. The first and second event signals may have different signal levels. For example, when the first event signals have a signal value of a logic high level, the second event signals may have a signal value of a logic low level. The controller 340 may determine whether the user 420 scans the target object by using the wireless probe 410 based on the signal levels of the event signals output by the detector 370.

FIGS. 5A through 5D are views of wireless probes 510, 520, 530, and 540 according to embodiments of the present invention, respectively. The alarm unit 380 may output alarm signals that allow a user to recognize a change in a power supply state when the power supply state of at least one of the first power, the second power, and the third power is changed.

Figure 5A:
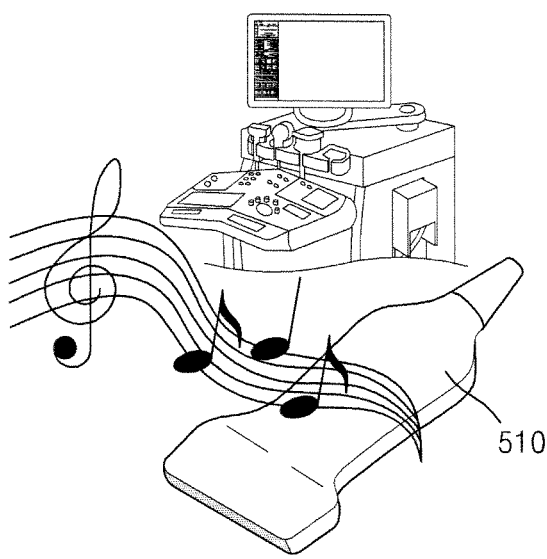
FIGS. 5A through 5D are views of wireless probes according to embodiments of the present invention, respectively.

Referring to FIG. 5A, the wireless probe 510 may output an alarm sound indicating that the power supply state of at least one of the first power, the second power, and the third power is changed via a speaker included in the alarm unit 380.

For example, when the first power, which is supplied to the ultrasound reception/transmission module 310, is blocked because scanning of the target object is finished, the speaker included in the alarm unit 380 may output an alarm sound. When the second power, which is supplied to the signal processing module 320, is blocked because the scanning of the target object and ultrasound data processing are finished, the speaker may output two alarm sounds. Also, when the second time passes after the scanning of the target object is finished, the speaker may output three alarm sounds. After three alarm sounds are output, the wireless probe 510 may be immediately turned off.

Also, the alarm sounds output by the alarm unit 380 may be different from one another because the alarm sounds are output according whether the power is supplied to the wireless probe 510.

Figure 5B:
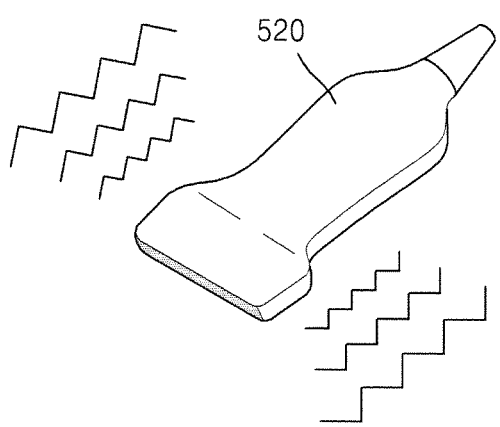

Referring to FIG. 5B, the wireless probe 520 may generate physical vibrations indicating that the power supply state of at least one of the first power, the second power, and the third power is changed via a vibrator included in the alarm unit 380.

For example, when the first power, which is supplied to the ultrasound reception/transmission module 310, is blocked because the scanning of the target object is finished, the vibrator may output one vibration. When the second power, which is supplied to the signal processing module 320, is blocked because the scanning of the target object and the ultrasound data processing are finished, the vibrator may output two vibrations. Furthermore, when the second time passes after the scanning of the target object is finished, the vibrator may output vibrations.

The vibrator may generate vibrations having different vibration times according to whether the power is blocked.

Figure 5C:
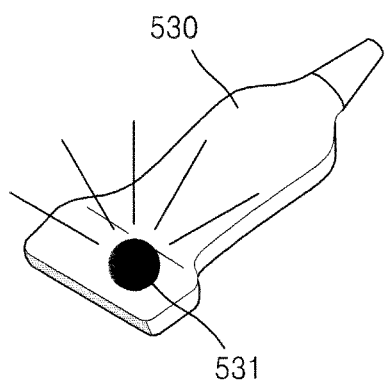

Referring to FIG. 5C, the wireless probe 530 may turn on lights indicating a change in the power supply state of at least one of the first power, the second power, and the third power via a lamp 531 included in the alarm unit 380.

For example, the lamp 531 is lit once when the first power is blocked supplied to the ultrasound reception/transmission module 310 because the scanning of the target object is finished. The lamp 531 is lit twice when the second power is blocked supplied to the signal processing module 320 because the scanning of the target object and the ultrasound data processing are finished. In addition, the lamp 531 is lit three times when the second time passes after the scanning of the target object is finished.

The lamp 531 may be lit with different colors according to whether the power is blocked.

Figure 5D:
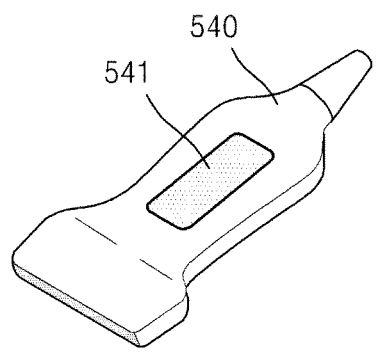

Referring to FIG. 5D, the wireless probe 540 may output a screen indicating a change in the power supply state of at least one of the first power, the second power, and the third power via a user interface screen displayed on a display panel 541.

The user interface screen indicating the power supply state and the change in the power supply state will be described in detail with reference to FIGS. 6 through 9.

Figure 6A:
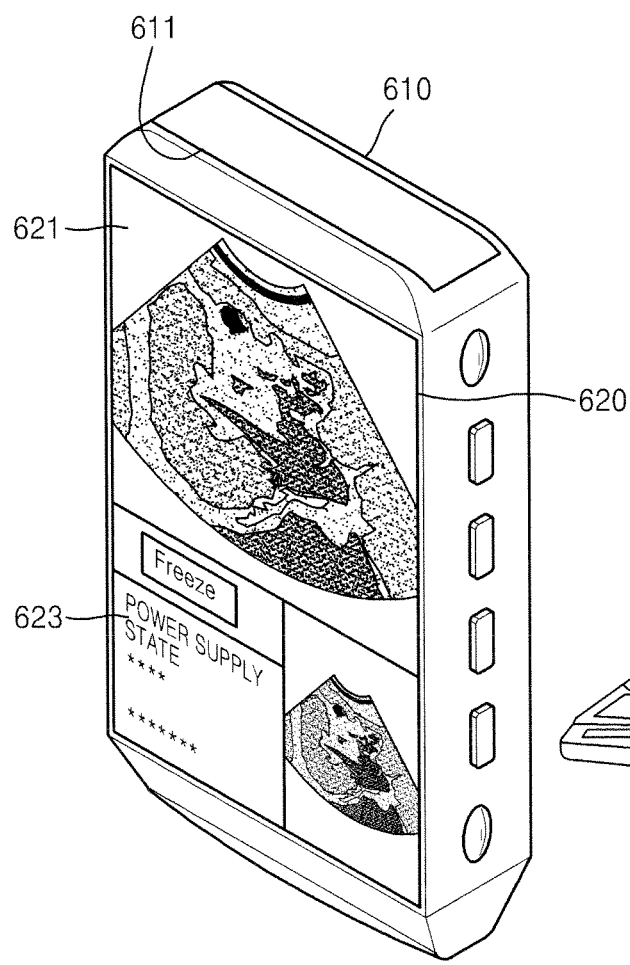
FIGS. 6A and 6B are views of a wireless probe according to another embodiment of the present invention.
Figure 6B:
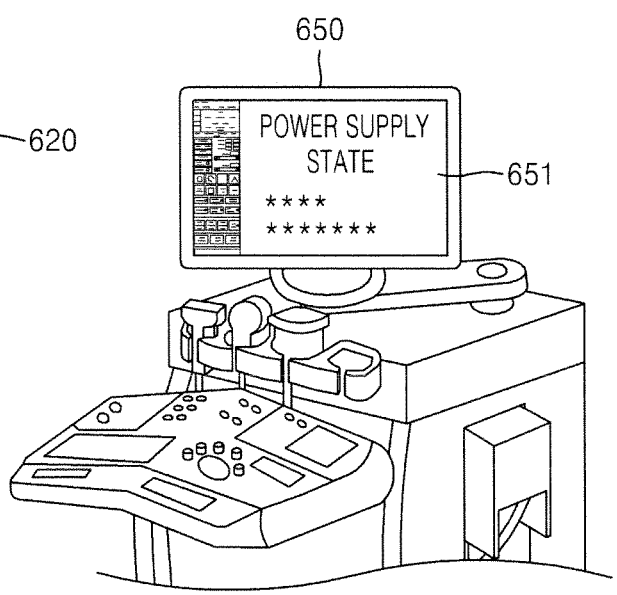

FIGS. 6A and 6B are views of a wireless probe 610 according to another embodiment of the present invention.

The wireless probe 300 includes the display 360 and may display a user interface screen indicating the power supply state and/or the change in the power supply state via the display panel (not shown) of the display 360. The user interface screen may be generated by the controller 340 or the user interface unit 390.

Referring to FIG. 6A, the wireless probe 610 corresponds to the wireless probe 300 of FIG. 3. A screen 620 displayed on a display panel of the wireless probe 610 includes a user interface screen 623 indicating a power supply state. Also, the screen 620 may further include an ultrasound image 621 showing the scanned target object. The ultrasound image 621 is an image generated by using the ultrasound data obtained in the ultrasound reception/transmission module 310.

Also, the user interface screen 623 may output a message indicating the change of the power supply state when the power supply state of at least one of the first power, the second power, and the third power is changed.

Referring to FIG. 6B, a medical device 650 is a medical device that may be connected to the wireless probe 300 via a wireless network and may receive data from the wireless communication module 330 of the wireless probe 300.

The controller 340 of the wireless probe 300 may transmit information about the power supply states of the first power, the second power, and the third power to the medical device 650. In addition, the controller 340 may transmit information about a change in the power supply state of at least one of the first power, the second power, and the third power to the medical device 650. Also, the controller 340 generates a user interface screen indicating the power supply state or the change in the power supply state and corresponding to the user interface screen 623 and may transmit the generated user interface screen to the medical device 650. Also, the wireless probe 300 may transmit information about the power supply state to the medical device 650 at a predetermined period. The wireless probe 300 may update the information about the power supply state and may transmit the updated information to the medical device 650 when the power supply state is changed.

Then, the medical device 650 may display a user interface screen 651 indicating the power supply state of the wireless probe 300 and/or the change in the power supply state based on at least one of information about the power supply state, information about the change in the power supply state, and the user interface screen 651 which are transmitted by the wireless probe 300.

Accordingly, the user may easily recognize the power supply state of the first power, the second power, and the third power of the wireless probe 300.

Figure 7:
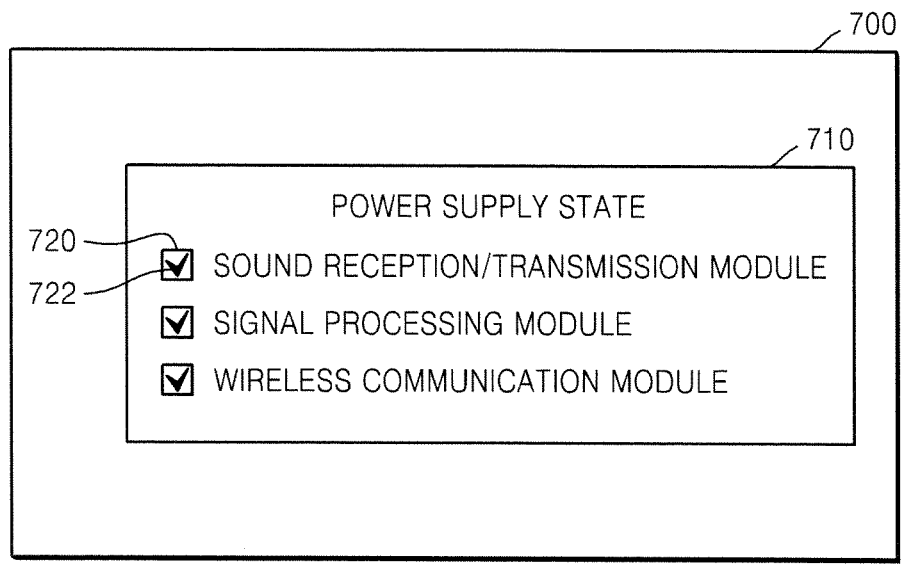
FIG. 7 is a view of a user interface screen displaying a power state of a wireless probe according to another embodiment of the present invention.

FIG. 7 is a view of a user interface screen 710 displaying the power state of the wireless probe 610 according to another embodiment of the present invention. Referring to FIG. 7, a screen 700 is displayed on at least one of the wireless probe 610 and the medical device 650 and includes the user interface screen 710.

Referring to FIG. 7, the user interface screen 710 displays the power supply states of the ultrasound reception/transmission module 310, the signal processing module 320, and the wireless communication module 330 included in the wireless probe 610.

For example, when an item 720 indicating the power supply state of a predetermined module is marked by a check cursor 722, it means that the power is supplied to the predetermined module corresponding to the item 720. Referring to the FIG. 7, the power is supplied to the ultrasound reception/transmission module 310, the signal processing module 320, and the wireless communication module 330.

Also, the user interface screen 710 may include information about the remaining amount of power of the power unit 350 (not shown). Although not illustrated in the user interface screen 710 of FIG. 7, the user interface screen 710 may include information about the current remaining amount of power, for example, 'the amount of battery power: 70%'.

Although not illustrated in the user interface screen 710 of FIG. 7, the user interface screen 710 may include menus for manually adjusting the power supply state of each of the ultrasound reception/transmission module 310, the signal processing module 320, and the wireless communication module 330. Also, the user interface screen 710 may display the amount of power consumed by each of the ultrasound reception/transmission module 310, the signal processing module 320, and the wireless communication module 330. Therefore, the user may selectively block the power supplied to a module that currently consumes a lot of power.

Figure 8:
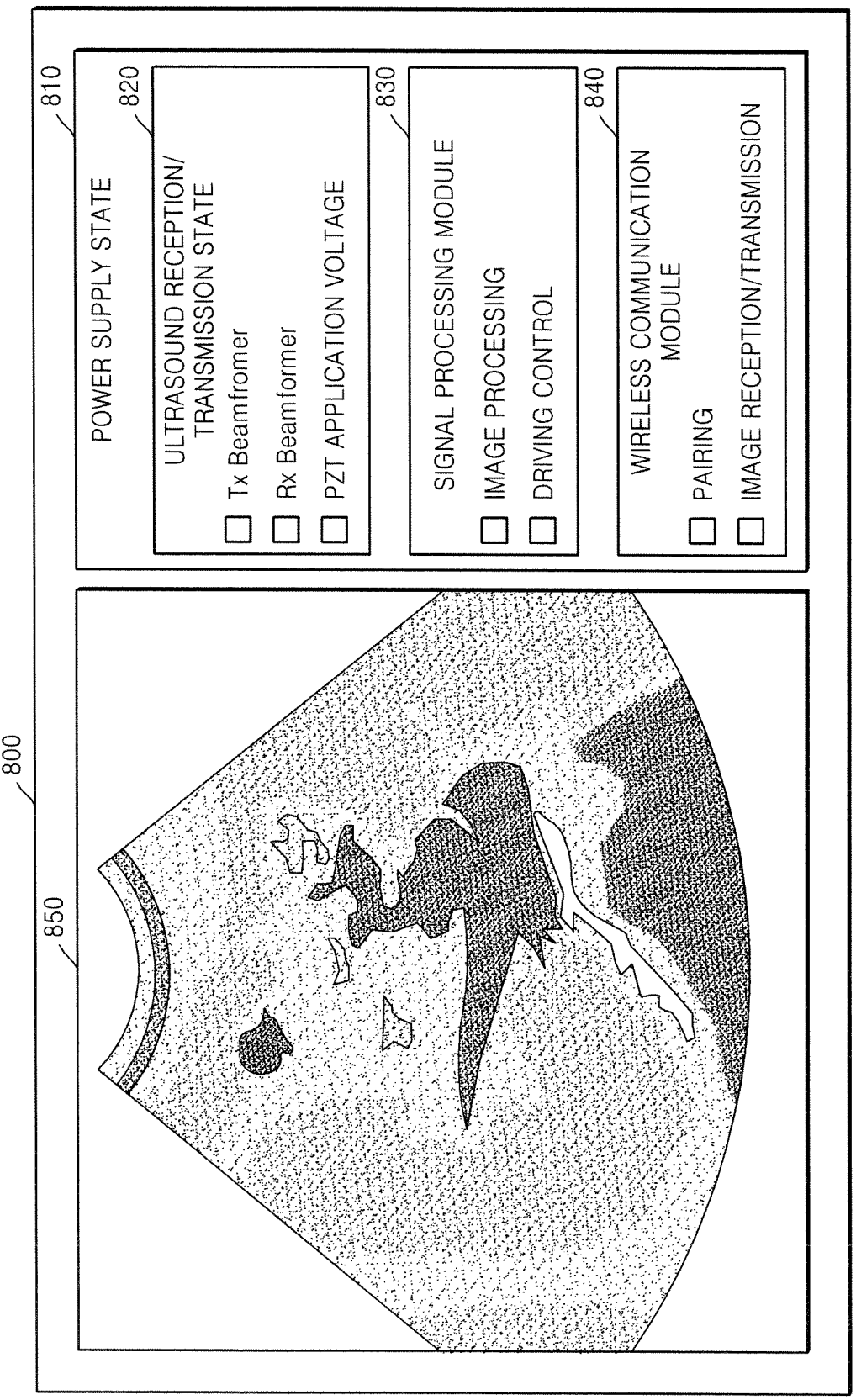
FIG. 8 is a view of a user interface screen displaying a power state of a wireless probe according to another embodiment of the present invention.

FIG. 8 is a view of a user interface screen 810 displaying the power state of the wireless probe 610 according to another embodiment of the present invention. Referring to FIG. 8, a screen 800 is displayed on at least one of the wireless probe 610 and the medical device 650 and includes the user interface screen 810.

Referring to FIG. 8, the screen 800 may further include an ultrasound image 850 showing the target object scanned by the ultrasound reception/transmission module 310.

Referring to FIG. 8, the user interface screen 810 may include a first item 820 indicating the power supply state of the ultrasound reception/transmission module 310, a second item 830 indicating the power supply state of the signal processing module 320, and a third item 840 indicating the power supply state of the wireless communication module 330.

Also, each item (for example, the first item 820) includes a sub-item with regard to at least one power necessary to operate each module and may display a power supply state. For example, the power necessary to operate the ultrasound reception/transmission module 310 may be the sound transmission beam-forming power for generating the transmit-focused ultrasound signals which is indicated as 'Tx Beamformer', power for driving a piezoelectric device (PZT) of the transducer 315 which is indicated as 'PZT application power', the sound reception beam-forming power for generating the received and focused ultrasound signals which is indicated as 'Rx Beamformer', etc.

Referring to FIG. 8, the first item 820 may display the power supply state of each of the sound transmission beam-forming power, the PZT application power, and the sound reception beam-forming power.

Figure 9:
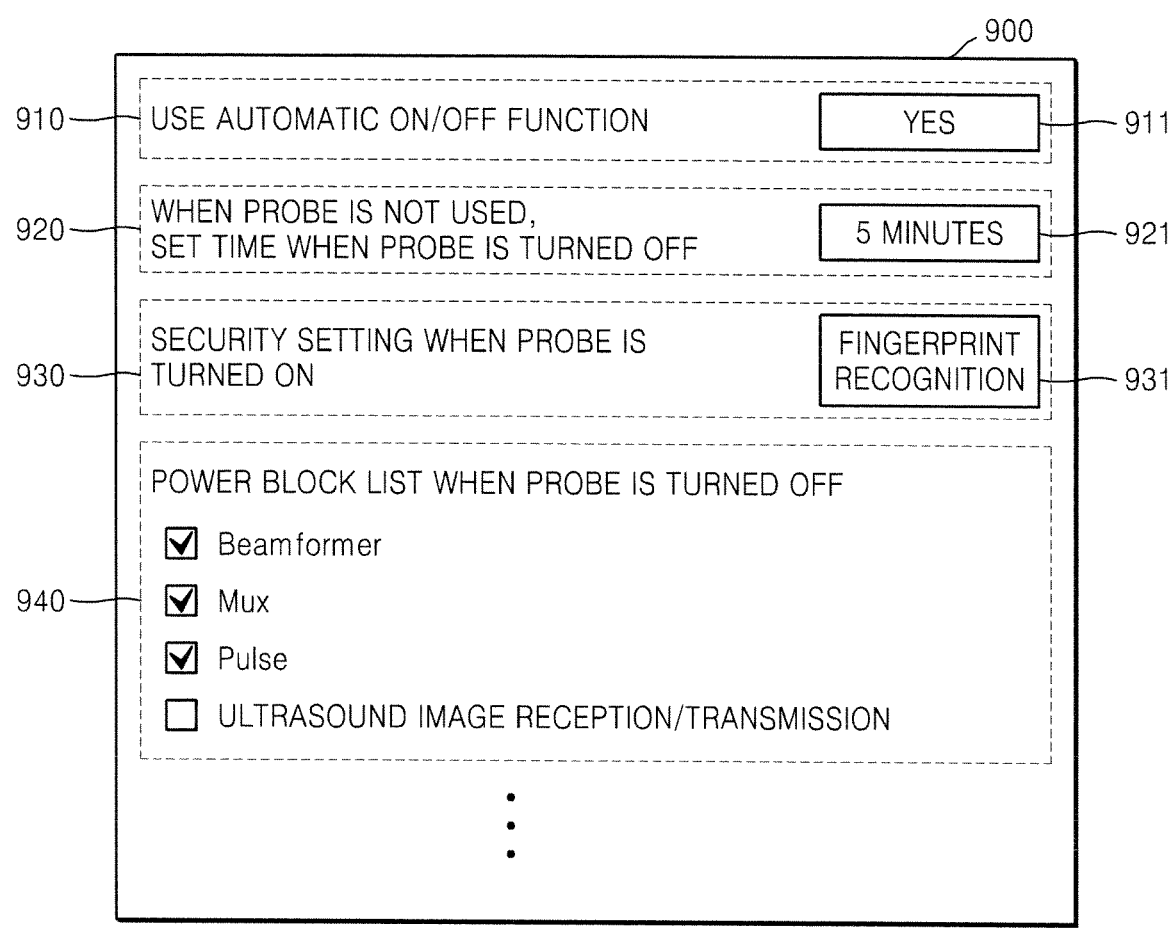
FIG. 9 is a view of a user interface screen for setting power of a wireless probe, according to an embodiment of the present invention.

FIG. 9 is a view of a user interface screen 900 for setting the power of the wireless probe 300, according to an embodiment of the present invention.

Referring to FIG. 9, the display 360 may display the user interface screen 900 used to set the supply of at least one of the first power, the second power, and the third power. In particular, the user interface screen 900 may include an item 910 including a menu key 911 for setting whether the controller 340 uses an 'automatic on/off function' that controls the supply of at least one of the first power, the second power, and the third power.

Moreover, the user interface screen 900 may include an item 920 including a menu key 921 for setting a point in time when the wireless probe 300 is turned off while the user does not manipulate the wireless probe 300. The user may separately set at least one of the first power, the second power, and the third power through the user interface screen 900.

When the wireless probe 300 is turned on, the controller 340 may set security settings for determining whether to allow the manipulation of the wireless probe 300.

The wireless probe 300 may be manipulated by anyone due to the portability of the wireless probe 300. Therefore, the controller 340 may set the wireless probe 300 to be manipulated by authorized persons and allows the authorized persons to manipulate the wireless probe 300.

The controller 340 may output the user interface screen 900 including a security setting menu for allowing the authorized persons to manipulate the wireless probe 300 when the wireless probe 300 is turned on.

When the wireless probe 300 is turned on, the controller 340 receives an input of at least one of text information such as passwords, patterns, and fingerprints through the security setting menu and determines whether the input of at least one of text information such as passwords, patterns, and fingerprints is the same as registered text information, patterns, and fingerprints. Then, when the input of at least one of text information such as passwords, patterns, and fingerprints is the same as the registered text information, patterns, and fingerprints, the controller 340 may allow the user to manipulate the wireless probe 300. Also, when the wireless probe 300 is turned on, the controller 340 outputs the security setting menu that notifies the security settings and performs biometric information recognition such as face recognition and iris recognition. Then, when the recognized biometric information is the same as registered biometric information, the controller 340 may allow the user to manipulate the wireless probe 300.

Also, when the security setting is performed by using the text information, the patterns, and the fingerprints, the controller 340 may output the user interface screen 900 for receiving inputs of the text information, the patterns, and the fingerprints through the display 360 and may receive the inputs of the text information, the patterns, and the fingerprints through the output user interface screen 900.

In addition, when the security setting is performed by the biometric information recognition such as the face recognition and the iris recognition, the wireless probe 300 may further include a biometric information camera (not shown) for recognizing the biometric information. In this case, the controller 340 receives recognition results through the biometric information camera and may determine whether the received recognition results are the same as registered information.

The user interface screen 900 may include an item 930 including a menu key 931 for determining whether to set the security settings.

The user interface screen 900 may further include an item 940 that indicates the power supply state of each component included in the wireless probe 300.

Figure 10:
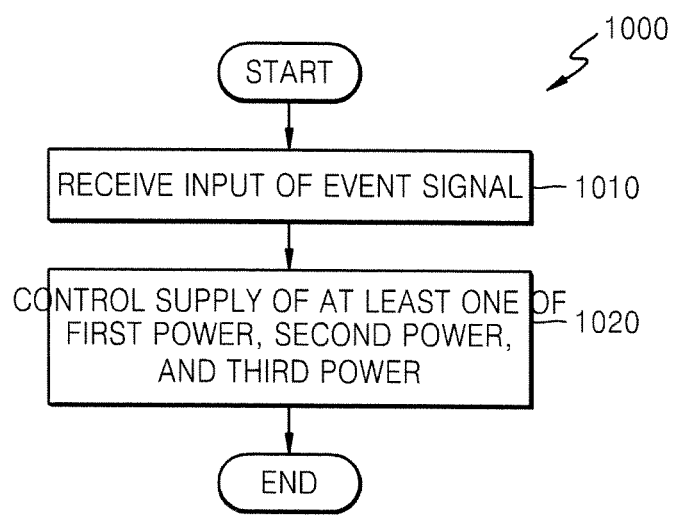
FIG. 10 is a flowchart of a method of controlling power of a wireless probe, according to an embodiment of the present invention.

FIG. 10 is a flowchart of a method 1000 of controlling power of a wireless probe, according to an embodiment of the present invention. The method 1000 of controlling the power of the wireless probe may be applied to the wireless probes described with reference to FIGS. 1 through 9. Therefore, the descriptions of the wireless probes, for example, the wireless probe 300, will not be repeated. Also, the method 1000 of controlling the power of the wireless probe will be described with reference to the wireless probe 300 of FIG. 3.

In the method 1000 of controlling the power of the wireless probe 300, the operation state of the wireless probe 300 is recognized in operation 1010. Operation 1010 may be performed by the detector 370. The wireless probe 300 may receive the event signals detected by the detector 370. The operation state of the wireless probe 300 may be recognized based on the input event signals.

In operation 1020, at least one of the first power supplied to the ultrasound reception/transmission module 310, which scans the target object by transmitting the ultrasound signals to the target object and receiving the ultrasound echo signals reflected from the target object, the second power supplied to the signal processing module 320, which generates the pulses for generating the ultrasound signals and generates the ultrasound data by using the ultrasound echo signals, and the third power supplied to the wireless communication module 330, which receives/transmits the data from/to the medical device, may be controlled based on the operation state of the wireless probe 300. Operation 1020 may be performed by the controller 340.

Furthermore, in operation 1020, the controller 340 may selectively supply or block each of the first power, the second power, and the third power based on the operation state of the wireless probe 300.

As described above, the method 1000 of controlling the power of the wireless probe 300 may minimize the power consumption of the wireless probe 300 by classifying the power consumed by and supplied to the wireless probe 300 and by selectively supplying or blocking the first power, the second power, and the third power based on the operation state of the wireless probe 300.

It should be understood that the exemplary embodiments described therein should be considered in a descriptive detect only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A wireless probe comprising:
a power unit configured to supply a first power, a second power, and a third power;
an ultrasound reception and transmission module configured to receive the first power, and by using the first power, transmit ultrasound signals to the target object and receive ultrasound echo signals reflected from the target object by using at least one transducer;
a signal processing module, including at least one processor, configured to receive the second power, and by using the second power, generate pulses for generating the ultrasound signals, transmit the generated pulses to the ultrasound reception and transmission module, and generate ultrasound data by using the ultrasound echo signals;
a wireless communication module configured to receive the third power, and by using the third power, receive data from a medical device, and transmit data to the medical device;
a controller configured to control supply of at least one of the first power, the second power, and the third power based on operation states of the wireless probe; and
a detector configured to detect whether a user manipulates the wireless probe,
wherein the controller, including at least one processor, is further configured:
to block the first power and the second power and supply the third power, when manipulation of the wireless probe is not detected by the detector for a first time period,
to block the first power, the second power, and the third power, when manipulation of the wireless probe is not detected by the detector for a second time period while blocking the first power and the second power and supplying the third power, and
to supply the first power, the second power, and the third power, when manipulation of the wireless probe is detected by the detector.

2. The wireless probe of claim 1, wherein the controller is configured to supply the first power, the second power, and the third power, when the wireless probe performs scanning.

3. The wireless probe of claim 1, wherein the controller is configured to block the first power and to supply at least one of the second power and the third power, when the wireless probe finishes performing scanning.

4. The wireless probe of claim 3, wherein the controller is configured to block the first power and to supply the second power and the third power, when the wireless probe finishes performing the scanning while processing the ultrasound data.

5. The wireless probe of claim 3, wherein the controller is configured to block the first power and the second power and to supply the third power, when the wireless probe finishes performing the scanning and processing ultrasound data.

6. The wireless probe of claim 1, wherein the controller is configured to block the first power, the second power, and the third power and to allow the wireless probe to be in a standby state, when the manipulation of the wireless probe is not detected for the second time period.

7. The wireless probe of claim 1, wherein the controller is configured to block the first power, the second power, and the third power and to turn off the wireless probe, when manipulation of the wireless probe is not detected for a third time period.

8. The wireless probe of claim 1, wherein the detector comprises at least one of a gyro sensor, a position sensor, an acceleration sensor, a temperature sensor, and a pressure sensor.

9. The wireless probe of claim 1, wherein the detector is configured to generate a first event signal having a first signal level and to transmit the generated first event signal to the controller, when it is determined that the wireless probe is scanning the target object based on detection results of the detector.

10. The wireless probe of claim 1, wherein the ultrasound reception and transmission module comprises:
the at least one transducer configured to generate the ultrasound signals when a predetermined voltage is applied;
an ultrasound generator configured to transmit driving signals for generating the ultrasound signals to the at least one transducer; and
an ultrasound receptor configured to receive and focus the ultrasound echo signals transmitted by the at least one transducer.

11. The wireless probe of claim 10, wherein the first power comprises at least one of power for supplying the predetermined voltage, ultrasound transmission beam-forming power for generating transmit-focused ultrasound signals, and sound reception beam-forming power for generating the ultrasound echo signals that are received and focused.

12. The wireless probe of claim 10, wherein the second power comprises at least one of power for generating the pulses, and power used to process at least one of the ultrasound data and an ultrasound image corresponding to the ultrasound data.

13. The wireless probe of claim 1, wherein the third power comprises at least one of pairing power used to link the wireless probe with the medical device, and power used to adjust a sensitivity of signals for receiving/transmitting the predetermined data.

14. The wireless probe of claim 1, wherein the controller is configured to generate information about a power supply state of at least one of the first power, the second power, and the third power and to transmit the information to the medical device.

15. The wireless probe of claim 1, further comprising a display configured to display a user interface screen indicating power supply states of the first power, the second power, and the third power.

16. The wireless probe of claim 1, further comprising a display configured to display a user interface screen used to set a power supply of at least one of the first power, the second power, and the third power.

17. The wireless probe of claim 1, further comprising an alarm device configured to output alarm signals for allowing a user to recognize a change in a power supply state of at least one of the first power, the second power, and the third power, when the power supply state of the at least one of the first power, the second power, and the third power is changed.

18. The wireless probe of claim 17, wherein the alarm device comprises at least one of a speaker, a lamp, a vibrator, and a display.

19. The wireless probe of claim 1, wherein the controller is configured to output a user interface screen including a security setting menu for allowing manipulation of the wireless probe when the wireless probe is turned on.

20. The wireless probe of claim 1, wherein the power unit is configured to charge power and comprises a battery configured to supply at least one of the first power, the second power, and the third power by using the charged power.

21. The wireless probe of claim 1, wherein the power unit is configured to receive wireless power from the outside and supplies at least one of the first power, the second power, and the third power by using the received wireless power.

22. The wireless probe of claim 1, wherein the second time period is greater than the first time period.

23. A method of controlling power of a wireless probe, the method comprising:
supplying a first power, a second power, and a third power;
recognizing, by a detector, manipulation of the wireless probe; and
controlling, by a controller, at least one of the first power supplied to an ultrasound reception and transmission module, which scans a target object by transmitting ultrasound signals to the target object and receiving ultrasound echo signals reflected from the target object, the second power supplied to a signal processing module, which generates pulses for generating the ultrasound signals and generates ultrasound data by using the ultrasound echo signals, and the third power supplied to a wireless communication module, which receives data from a medical device and transmits data to the medical device based on the operation state of the wireless probe,
wherein the controlling of the at least one of the first power, the second power, and the third power comprises:
when manipulation of the wireless probe is not detected by the detector for a first time period, blocking the first power and the second power, and supplying the third power, and
when manipulation of the wireless probe is not detected by the detector for a second time period while blocking the first power and the second power and supplying the third power, blocking the first power, the second power, and the third power, and when manipulation of the wireless probe is detected by the detector, supplying the first power, the second power, and the third power.

24. The method of claim 23, wherein the second time period is greater than the first time period.

\* \* \* \* \*